(12) United States Patent
Aporva

(10) Patent No.: US 12,251,089 B2
(45) Date of Patent: Mar. 18, 2025

(54) AUTOMATED FLUID DISPENSER WITH DRIVER AND DISPOSABLE PROBE

(71) Applicants: BAXTER INTERNATIONAL INC., Deerfield, IL (US); BAXTER HEALTHCARE SA, Glattpark (CH)

(72) Inventor: Raj M R Aporva, Shivamogga (IN)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 18/693,700

(22) PCT Filed: Sep. 15, 2022

(86) PCT No.: PCT/US2022/043675
§ 371 (c)(1),
(2) Date: Mar. 20, 2024

(87) PCT Pub. No.: WO2023/043934
PCT Pub. Date: Mar. 23, 2023

(65) Prior Publication Data
US 2024/0325009 A1    Oct. 3, 2024

(30) Foreign Application Priority Data
Sep. 20, 2021  (IN) .............................. 202141042483

(51) Int. Cl.
*A61B 17/00* (2006.01)
*A61B 90/98* (2016.01)

(52) U.S. Cl.
CPC ........ *A61B 17/00491* (2013.01); *A61B 90/98* (2016.02); *A61B 2017/00039* (2013.01); *A61B 2017/00199* (2013.01); *A61B 2017/00398* (2013.01)

(58) Field of Classification Search
CPC .............. A61B 17/00491; A61B 90/98; A61B 2017/00039; A61B 2017/00199; A61B 2017/00398
See application file for complete search history.

(56) References Cited

U.S. PATENT DOCUMENTS

| | | | |
|---|---|---|---|
| 2016/0166761 A1* | 6/2016 | Piehl | A61B 17/3498 604/207 |
| 2018/0085517 A1* | 3/2018 | Laurence | A61M 5/145 |
| 2019/0321837 A1* | 10/2019 | Bhogal | B05B 7/2429 |
| 2022/0313901 A1 | 10/2022 | Lane et al. | |

FOREIGN PATENT DOCUMENTS

| | | |
|---|---|---|
| EP | 3 848 069 | 7/2021 |
| WO | 20110143573 | 11/2011 |

(Continued)

OTHER PUBLICATIONS https://www.atlasrfidstore.com/rfid-insider/rfid-vs-nfc/ (Year: 2013).*
(Continued)

*Primary Examiner* — Tan-Uyen T Ho
*Assistant Examiner* — Khoa Tan Le
(74) *Attorney, Agent, or Firm* — K&L Gates LLP

(57) ABSTRACT

Example dispensing devices for applying a hemostatic agent or other sealant to a biological tissue.

5 Claims, 10 Drawing Sheets

(56) References Cited

FOREIGN PATENT DOCUMENTS

WO      20160138018      9/2016
WO      2020096587      5/2020

OTHER PUBLICATIONS

Search Report issued in International Patent Application No. PCT/US2022/043675 mailed on Dec. 19, 2022—4 pages.
Written Opinion issued in International Patent Application No. PCT/US2022/043675 mailed on Dec. 19, 2022—7 pages.
IPRP issued in International Patent Application No. PCT/US2022/043675 mailed on Aug. 8, 2023—6 pages.

\* cited by examiner

AUTOMATED FLUID DISPENSER WITH DRIVER AND DISPOSABLE PROBE

PRIORITY CLAIM

The present application is a national phase entry of PCT Patent Application No. PCT/US2022/043675, filed on Sep. 15, 2022, which claims priority to and the benefit of Indian Provisional Patent Application No. 20/2141042483, filed on Sep. 20, 2021, the entire contents of which are hereby incorporated by reference and relied upon.

BACKGROUND

Dispensing devices or dispensers are used to dispense controlled amounts of fluids. In a medical context, the dispensed fluids may include a biological sealant, such as a hemostatic matrix or other sealant, which is applied on a biological tissue as a tissue adhesive to control bleeding or reduce risks associated with blood clots. During cardiac surgeries or other surgeries that involve cutting/repairing blood vessels for example, there is an increased risk of forming blood clots that can potentially cause deep vein thrombosis or pulmonary embolism. A dispensing device can be used to mitigate these types of risks by dispensing a hemostatic matrix (or other sealant) on a blood vessel or other biological tissue.

Dispensers are commonly used in surgeries and in other medical procedures to apply biological sealants. Unfortunately, manual dispensers are burdensome to medical professionals. For example, a medical professional might accidentally trigger release of an incorrect amount of sealant from the manual dispenser. As another example, a surgeon might begin applying a sealant to a wound without realizing that the remaining amount of the sealant in the dispenser is not sufficient for adequately sealing the wound. It can be burdensome for the surgeon to evaluate how much sealant is available in the dispenser quickly and accurately, especially during a surgical procedure. A manual dispenser might also be accidentally used with more than one patient, which could pose a hazard to patients.

SUMMARY

The present disclosure provides a dispensing device or dispenser for dispensing and applying a sealant. The dispenser disclosed herein provides feedback about an amount of sealant currently available in the dispenser, which allows a user to more accurately and quickly evaluate whether a sufficient amount of sealant is present prior to (and/or while) dispensing the sealant. The dispenser also provides an enhanced triggering mechanism, which allows a user to more accurately control application of the sealant.

In an example, a dispensing device is disclosed that includes a driver unit and a probe unit. The probe unit is detachably mounted on the driver unit. The probe unit includes a housing configured to store a sealant, a near field communication (NFC) tag configured to wirelessly transmit information identifying the probe unit. The driver unit includes a display, a motor, a trigger, and a controller. The display is configured to display an identifier that identifies the probe unit based on the information received from the NFC tag. The trigger is configured to receive a tactile input. The motor is configured to cause the probe unit to dispense the sealant out of the housing based on the tactile input.

The dispensing device or dispenser disclosed herein is expected to offer convenience compared to devices and systems that require manually dispensing hemostatic agents and/or other sealants.

It is another advantage of the present disclosure to provide a dispensing device that includes a reusable driver unit and a disposable probe unit.

It is another advantage of the present disclosure to provide a sealant applicator (e.g., sealant applier) having a motor-assisted dispensing mechanism.

It is another advantage of the present disclosure to provide a dispensing system that provides feedback to a user about an amount of a sealant fluid available for dispensation by a probe unit and that displays an identifier of the probe unit when the probe unit is attached to the dispenser.

It is another advantage of the present disclosure to provide a dispenser configured to automatically actuate a sealant flowing through the dispenser according to one of a plurality of different modes depending on a tactile input received from a user.

Additional features and advantages of the disclosed sealant applicator (e.g., sealant dispenser), systems, and methods are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

DETAILED DESCRIPTION OF EXAMPLE EMBODIMENTS

Example sealant dispensing systems (e.g., sealant dispenser, hemostatic agent applicator, hemostatic matrix dispenser, etc.) herein provide improved hemostatic fluid application and dispensing features.

Figure 1:
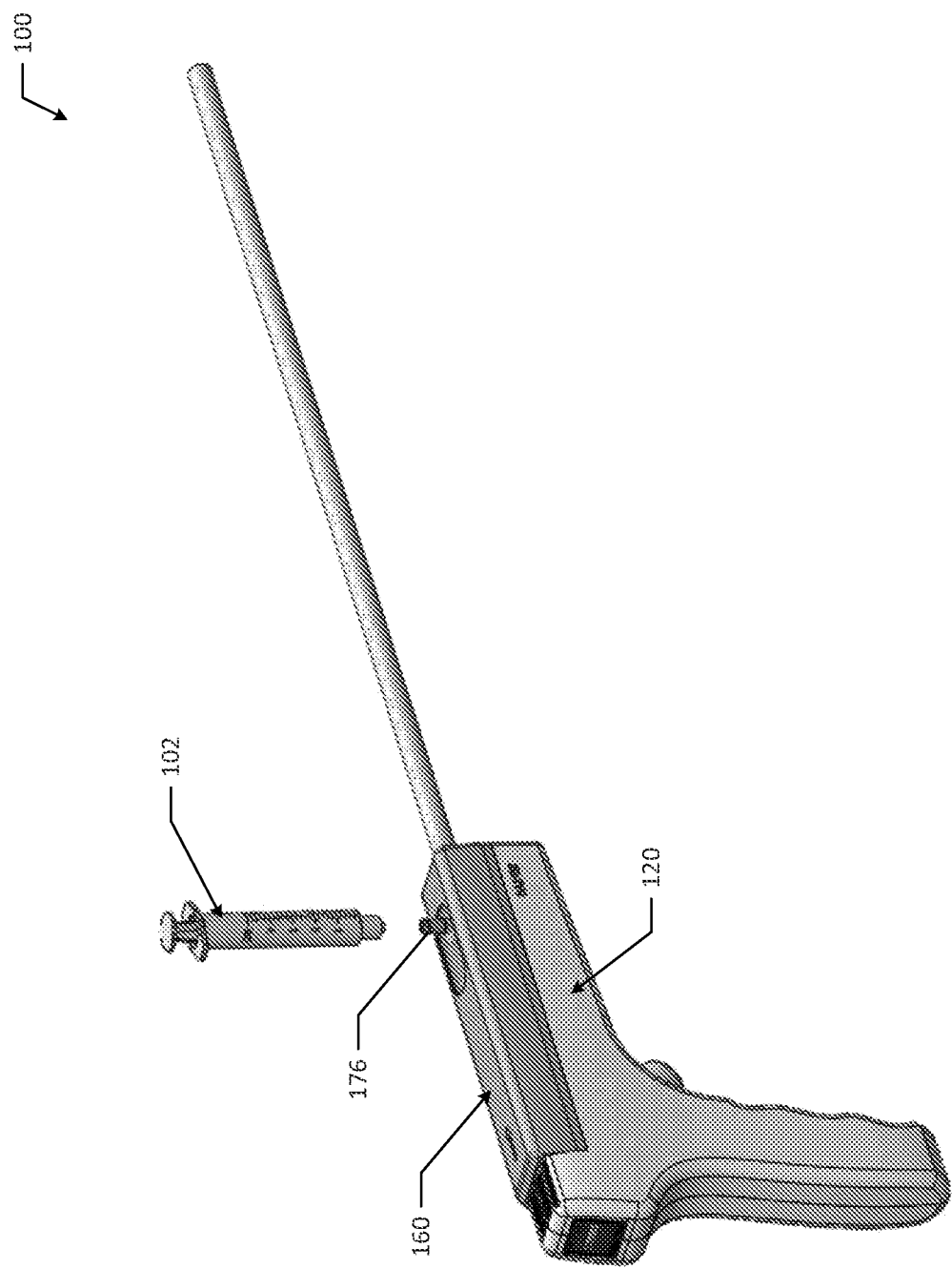
FIG. 1 is a perspective view of an example sealant dispenser that includes a disposable probe unit attached to a reusable driver unit, according to the present disclosure.
Figure 2:
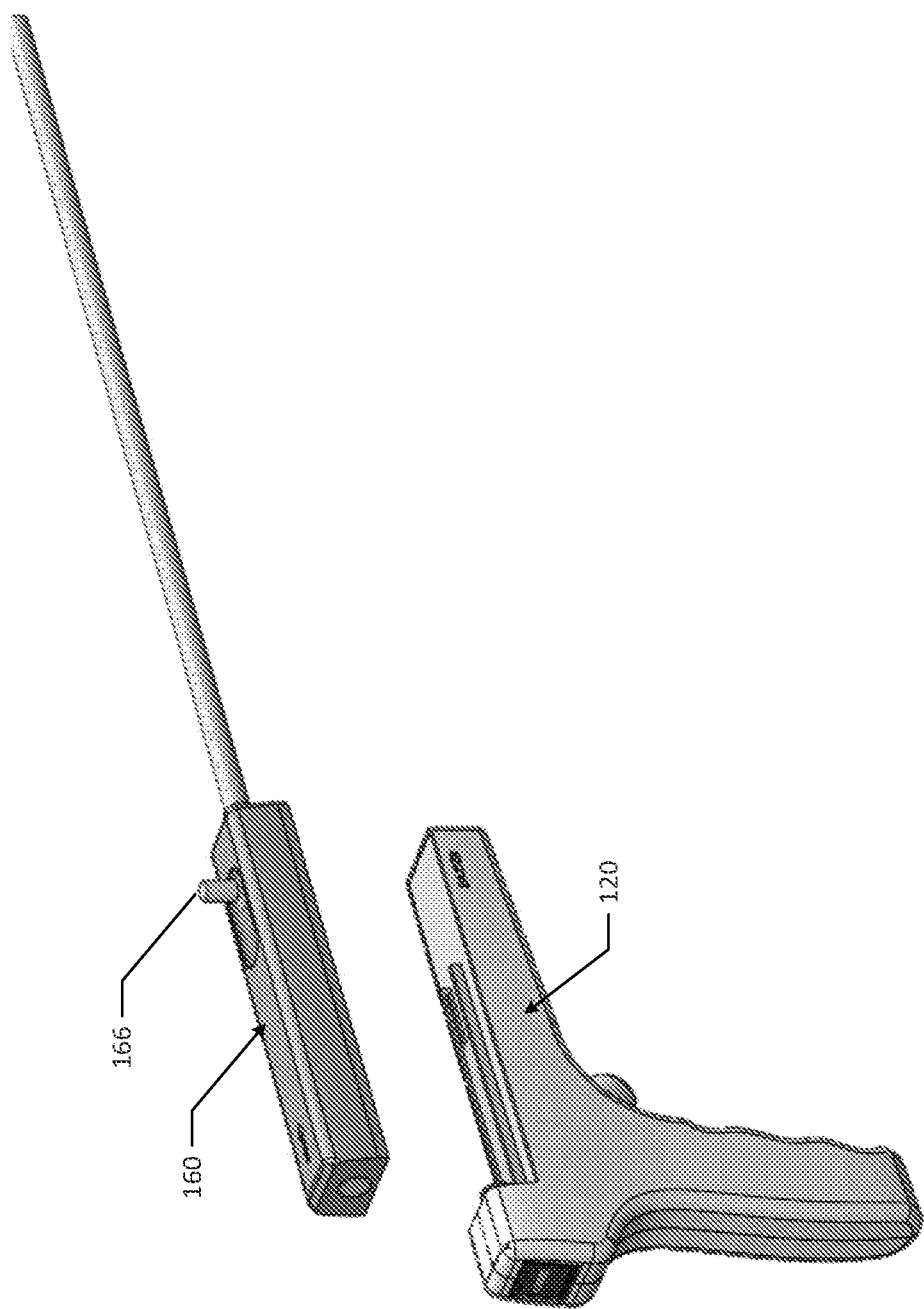
FIG. 2 is a perspective view of an example sealant dispenser in a configuration where an example probe unit is detached from an example driver unit, according to the present disclosure.

FIG. 1 illustrates an example fluid dispensing system or dispenser 100, according to the present disclosure. FIG. 2 illustrates the example dispenser 100 in a configuration where the disposable probe unit 160 is detached from (e.g., not mounted on) the driver unit 120. The dispenser 100 is configured to apply a sealant (e.g., a hemostatic matrix or other flowable hemostatic agent) to a surgical surface (e.g., blood vessel, etc.). The dispensing system 100 includes a filling syringe 102, a reusable driver unit 120, and a disposable probe unit 160.

The filling syringe 102 can be used to fill and/or refill a sealant reservoir (not shown) inside the probe unit 160. In specific examples, the filling syringe 102 can be a 5 milliliter (ml) or a 10 ml syringe. Other types of syringes are possible as well. To facilitate this, the probe unit 160 includes a valve 176 (shown in FIG. 1) shaped to receive the filling syringe 102. For example, the luer cap 166 (shown in FIG. 2) can be removably disposed on the probe unit 160 to expose or cover an inlet or port of the valve 176 to which the filling syringe can be connected to transport sealant fluid into the probe unit 160.

In some examples, the probe unit 160 is configured as a removable, detachable, and/or disposable device. For example, before or during a surgical procedure, a new disposable probe unit 160 can be installed on/attached to the driver unit 120. Then, in this example, the disposable probe unit 160 can be removed and disposed of after the surgical procedure. In general, it is desirable to avoid using a same endoscopic applicator (e.g., the probe unit 160) to treat multiple patients so as to avoid risks such as contamination or infection. To that end, the present disclosure provides the disposable probe unit 160 as a relatively low cost component that can be replaced without replacing the entire dispenser 100.

Figure 3A:
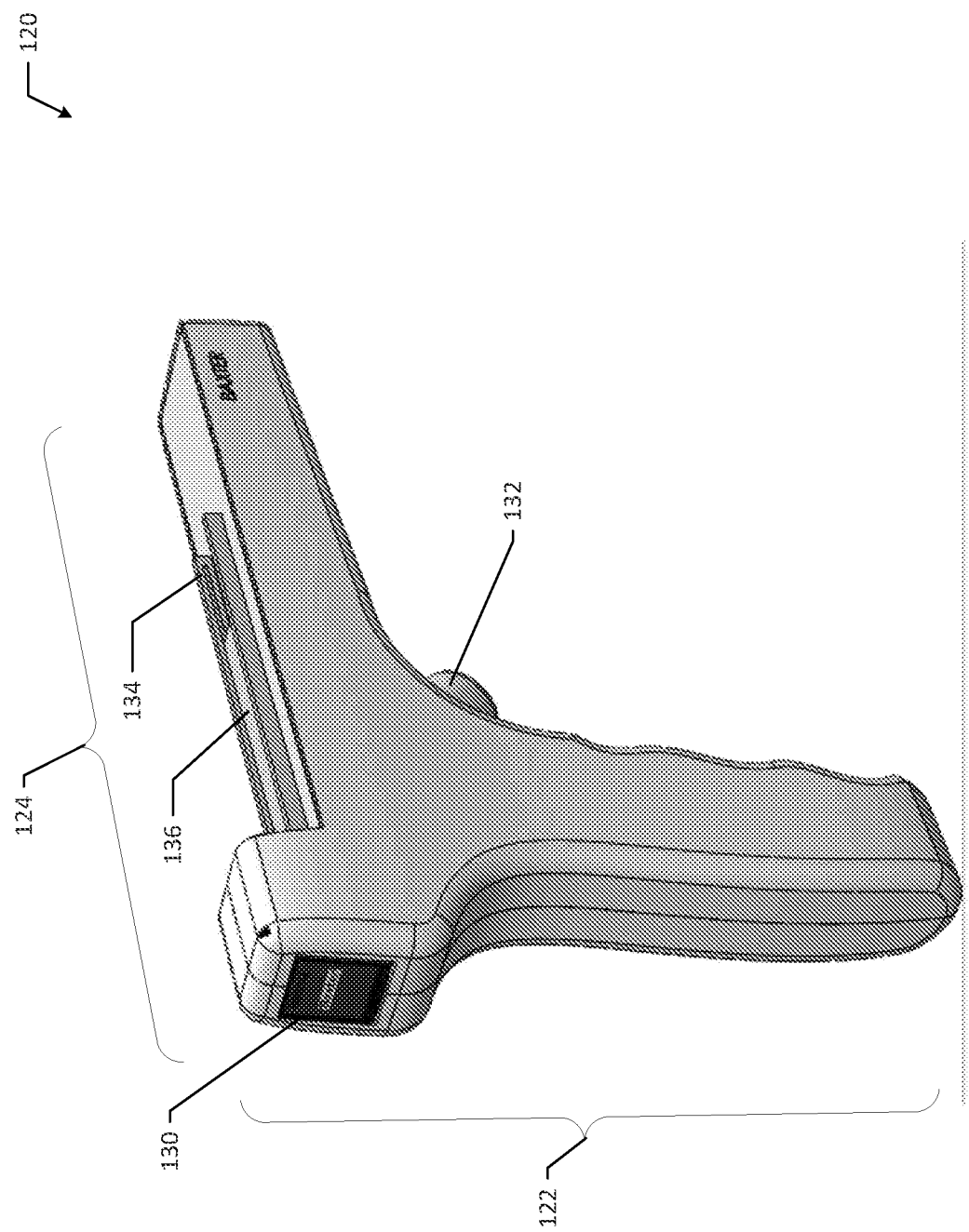
FIG. 3A is a perspective view of an example driver unit, according to the present disclosure.
Figure 3B:
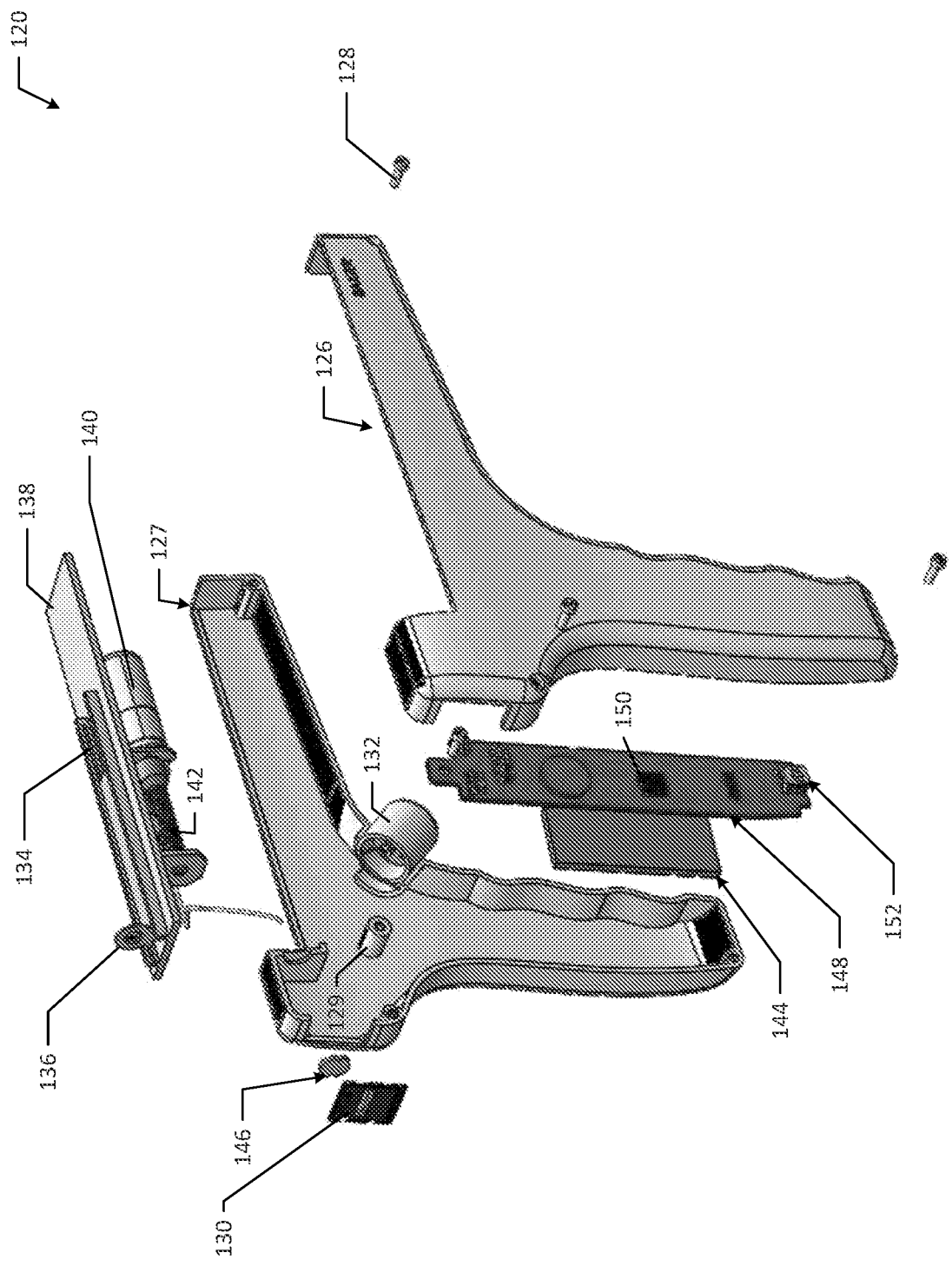
FIG. 3B is an exploded view of the example driver unit of FIG. 3A.

FIG. 3A is a perspective view of an embodiment of the example driver unit 120, according to the present disclosure. FIG. 3B is an exploded view of the example driver unit 120 of FIG. 3A.

In some examples, the driver unit 120 is configured as a reusable device that can receive, mount, and/or operate different disposable probe units similar to probe unit 160. As best shown in FIG. 3A, the driver unit 120 is shaped and configured as a hand-held device (e.g., gun shape). As such, the driver unit 120 (and more generally the dispenser 100) can be conveniently held and operated using a single hand during a surgery and/or while performing an endoscopic application of a sealant. In the illustrated example, the driver unit 120 is shaped to form a handle that can be used to support/grip the driver unit 120 (and/or the dispenser 100) with a single hand.

As shown, the driver unit 120 includes a display 130 and a trigger 132. In the illustrated example, the display 130 is disposed at a proximal end 122 of the driver unit 120. With this arrangement, the present disclosure advantageously allows a user to easily view information on the display 130 while holding the driver unit 120, applying sealant on a surgical site, and/or while performing some other surgical task.

In an example, the display 130 is configured to display a current level and/or amount of sealant (e.g., in milliliters) currently disposed inside the probe unit 160 (and/or currently available for dispensing). Thus, the dispenser 100 of the present disclosure can advantageously assist a surgeon when evaluating whether a sufficient amount of sealant is available for adequately sealing a wound.

In an example, the display 130 is configured to display operation parameters of the dispenser 100, such as a value of a fixed amount of sealant that will be dispensed when the trigger 132 detects a tactile input assigned to an automatic mode of the dispenser 100. For instance, a user of the dispenser 100 can select a value of one milliliter as the fixed amount to be dispensed when the user taps or presses the trigger 132 for a short period of time (e.g., 100 milliseconds). In this example, the display 130 may be configured to display the selected value of one millimeter to as a convenient reminder for the user during a surgical procedure.

In an example, the display 130 is configured to display an identifier (e.g., a number) that identifies which specific probe unit 160 is currently mounted on the driver unit 120. For instance, a given probe unit 160 can be configured to transmit a message (e.g., radio frequency identifier (RFID) code, etc.) when it is mounted on the driver unit 120, and the display 130 can then display a value representing an identifier that identifies that particular probe unit 160.

The display 130 may include any type of display, such as a light emitting diode (LED) display, a liquid crystal display (LCD), among others. In some examples, the display 130 is a touch screen display that allows a user to select, adjust, and/or set various operation parameters to control the driver unit 120 (and/or the dispenser 100). As an example, a user can use the touch screen display 130 to set a value for a particular amount of sealant (e.g., 1 ml, etc.) that the dispenser 100 should dispense when operating in an automatic mode.

The trigger 132 is configured to detect a tactile input, such as a touch or press action, from a user of the dispenser 100. In a specific example, the trigger 132 includes a silicon cover (or other cover) and a tactile switch covered by the silicon cover. The driver unit 120 is configured to control the probe unit 160 (and/or one or more components of the driver unit 120) based on the tactile input detected by the trigger 132. In a specific example, a force required to operate the trigger 132 can be relatively low (e.g., between 3 Newtons (N) and 12 N).

In an example, the driver unit 120 is configured to switch on or off the driver unit 120 (and/or the display 130) in response to trigger 132 detecting a first type of tactile input (e.g., a long press).

In an example, the driver unit 120 is configured to operate the dispenser 100 in a priming mode in response to the trigger 132 detecting a second type of tactile input (e.g., a certain pattern of presses). When operating in the priming mode for instance, the driver unit 120 can automatically operate the probe unit 160 to actuate a particular amount of sealant through a cannula of the probe unit 160 so as to prime the cannula.

In an example, the driver unit 120 is configured to operate the dispenser 100 in an automatic mode in response to the trigger 132 detecting a third type of tactile input (e.g., a soft press, short press, etc.). In the automatic mode, the driver unit 120 causes the probe unit 160 to dispense a fixed amount of sealant (e.g., one milliliter, half a milliliter, etc.)

In an example, the driver unit 120 is configured to operate the dispenser 100 in a manual mode in response to the trigger 132 detecting a fourth type of tactile input (e.g., a continuous or long press, a hard press, etc.). In the manual mode for instance, the driver unit 120 may cause the probe unit to continuously dispense sealant until a user of the dispenser 100 stops pressing the trigger 132.

Accordingly, the present disclosure advantageously enables a user of the dispenser 100 to conveniently and efficiently operate the dispenser 100 and/or dispense sealant fluid (e.g., hemostatic matrix) in a particular controlled manner with less effort as compared to traditional hemostatic agent dispensers.

As shown, the driver unit 120 also includes a rail 134 and a pusher 136 disposed at a top side 124 of the driver unit 120. The rail 134 is configured to provide a track for receiving and/or retaining the probe unit 160 when the probe unit 160 is mounted on the driver unit 120. The pusher or rack 136 is configured to actuate (e.g., by pushing or pulling a syringe plunger, etc.) the sealant out of the probe unit 160 when the trigger 132 is pressed by a user of the dispenser 100.

As best shown in FIG. 3B, the driver unit 120 includes a right cover 126, a left cover 127, a plurality of screws 128, and a plurality of inserts 129. During assembly, the right cover 126 and the left cover 127 are coupled (e.g., by aligning the screws 128 with the inserts 129) to form a frame that supports the various components of the driver unit 120 in a particular arrangement.

The driver unit 120 also includes a chassis 138, which can be formed from steel or other solid material. The rail 134 and the pusher 136 are disposed on a first side of the chassis 138. The driver unit 120 also includes a motor 140 and a worm shaft 142 is disposed on another side of the chassis 138 opposite the side where the rail 134 and the pusher 136 are disposed. The motor 140 is configured to actuate the pusher 136 (via the worm shaft 142) to move the pusher 136 forward or backward inside the rail or track 134.

In an example, the motor 140 actuates the pusher 136 to cause the probe unit 160 to dispense a sealant. The amount of sealant dispensed by the probe unit 160 (as well as the remaining amount of sealant) can be measured using an encoder (not shown) that measures the amount of actuation by the motor 140. As such, in line with the discussion above, the driver unit 120 can display the remaining amount of sealant in the probe unit 160 via the display 130.

The driver unit 120 also includes a battery 144, which can be a lithium polymer (LIPO) battery or any other battery. The battery 144 provides power for various components of the driver unit 120 (e.g., the display 130, the trigger 132, the motor 140, etc.).

The driver unit 120 also includes a hall sensor 146 disposed adjacent to the display 130 at the proximal end 122 of the driver unit 120. The hall sensor 146 is configured to detect a magnet (not shown) inside the probe unit 160. The driver unit 120 is configured to detect that the probe unit 160 is mounted on/attached to the driver unit 120 based on a signal from the hall sensor 146.

The driver unit 120 also includes circuitry 148 (e.g., one or more printed circuit boards (PCBs)) wired to perform the various functions and operations of the driver unit 120 as described above. For example, the driver unit 120 includes a controller 150 that receives and provides electrical signals to control various components of the driver unit 120 (e.g., the display 130, the trigger 132, the motor 140, the hall sensor 146, the battery 144, etc.) and thus cause the driver unit 120 (and/or each of the components thereof) to operate in accordance with the description above.

In an example, the controller 150 receives a signal from the hall sensor 146 indicating that a probe unit 146 is mounted on the driver unit 120. In response, the controller 150 operates a near field communication (NFC) reader (e.g., a component of the circuitry 148, etc.) to communicate with an NFC tag (not shown) of the probe unit 160 to retrieve identification information (e.g., NFC tag identifier, etc.) from the probe unit 160. The controller 150 then operates the display 130 to display an indication of the identifier of the probe unit 160 received from the NFC tag.

In an example, the controller 150 operates the trigger 132, in accordance with the description of the trigger 132 above, and receives a signal indicating detection of a tactile input by the trigger 132. Depending on the detected tactile input, the controller 150 then operates the motor 140, in accordance with the discussion above, to actuate the pusher 136 thereby causing the probe unit 160 to dispense sealant according to one of a plurality of operation modes. The controller 150 may also keep track of the amount of sealant dispensed and/or remaining in the probe unit 160 based on a measurement (e.g., via an encoder, etc.) of the actuation caused by the motor 140. The controller 150 may then operate the display 130 to update and/or display the current remaining amount of sealant inside the probe unit 160. More generally, the controller 150 is configured to operate the various components of the driver unit 120 to cause the driver unit 120 to perform the various functions and operations described above.

In an example, the controller 150 includes one or more processors and a memory storing instructions that, when executed by the one or more processors, cause the driver unit 120 (and/or components thereof) to perform the functions and operations described above. Alternatively or additionally, the controller 150 includes digital and/or analog circuitry wired to cause the driver unit 120 (and/or components thereof) to perform the functions and operations described above.

The driver unit 120 also includes a universal serial bus (USB) connector 152 coupled to the circuitry 148. The USB connector 152 is configured as an electrical interface between the driver unit 120 and an external device (e.g., battery charger, etc.). In an example, the USB connector 152 is configured to removably connect with a battery charger to receive power for charging the battery 144. In an example, the USB connector 152 is configured to connect with another USB-enabled external device (e.g., computer, etc.) to communicate with and/or receive instructions from the external device. For instance, the external device can communicate with the controller 150 (via the USB connector 152) to update software and/or firmware used to operate the driver unit 120 (and/or one or more components thereof).

Figure 3C:
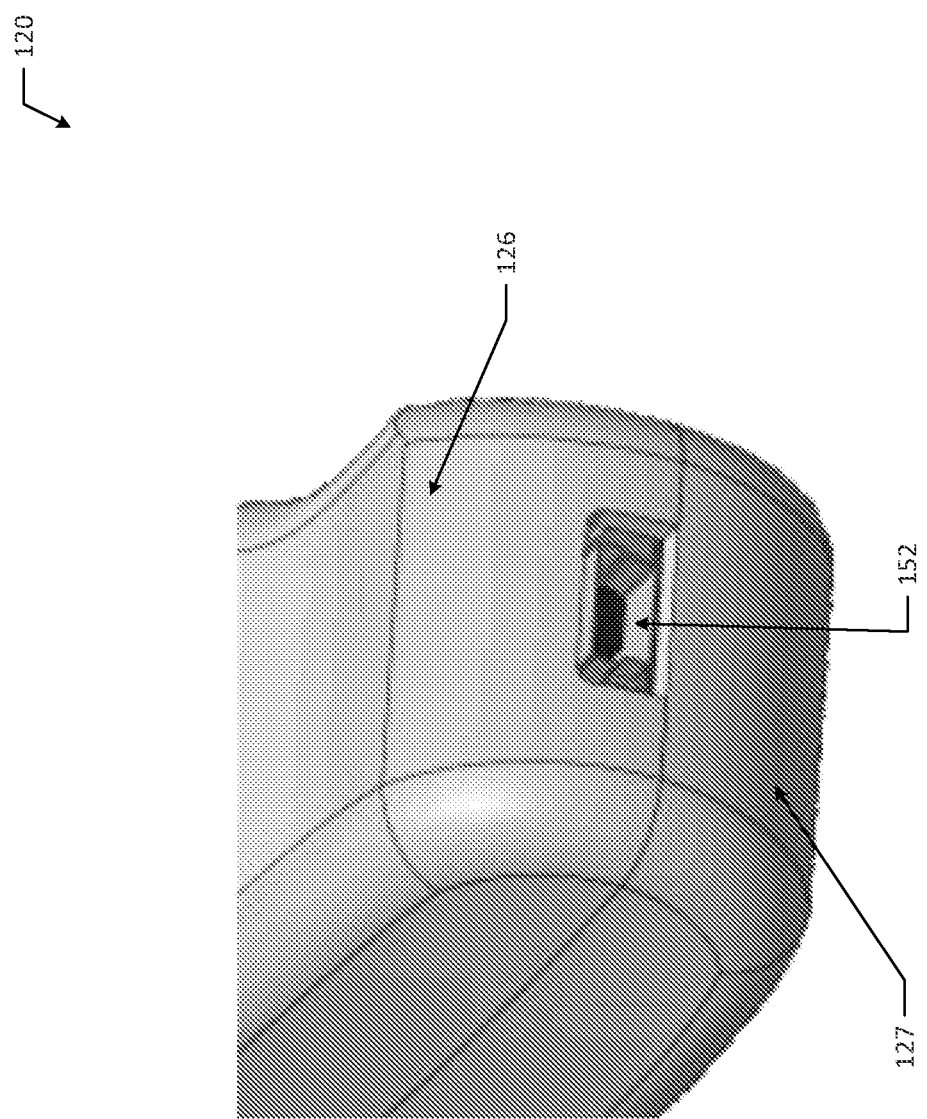
FIG. 3C is a perspective view of a portion of the example driver unit of FIG. 3A.

FIG. 3C is a perspective view of a portion of the driver unit 120 (e.g., bottom side). As best shown in FIG. 3C, the USB connector 152 is exposed to an external environment of the driver 120 when the driver unit 120 is assembled (i.e., when the right cover 126 and the left cover 127 are connected).

Figure 4A:
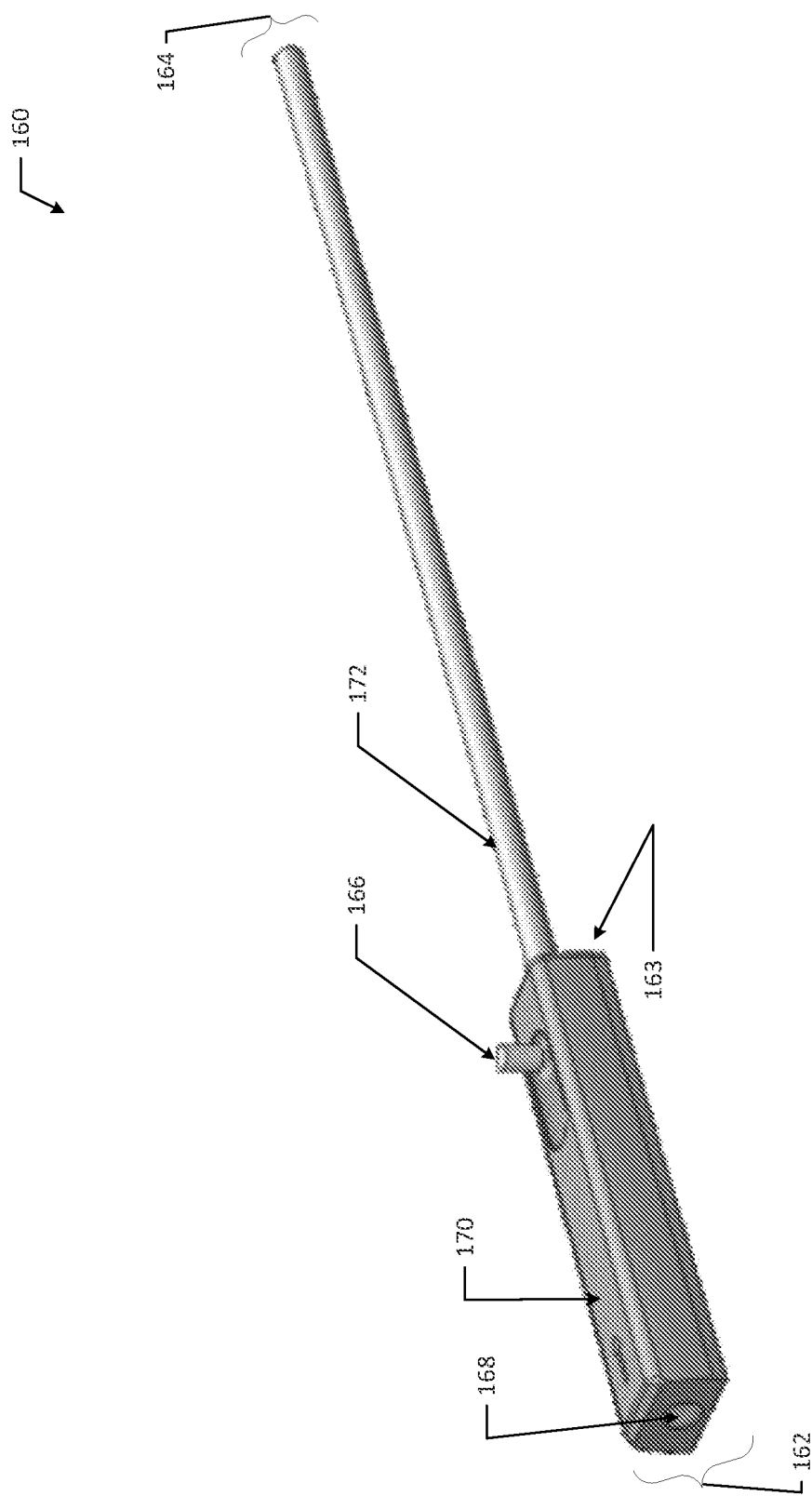
FIG. 4A is a perspective view of an example probe unit, according to the present disclosure.
Figure 4B:
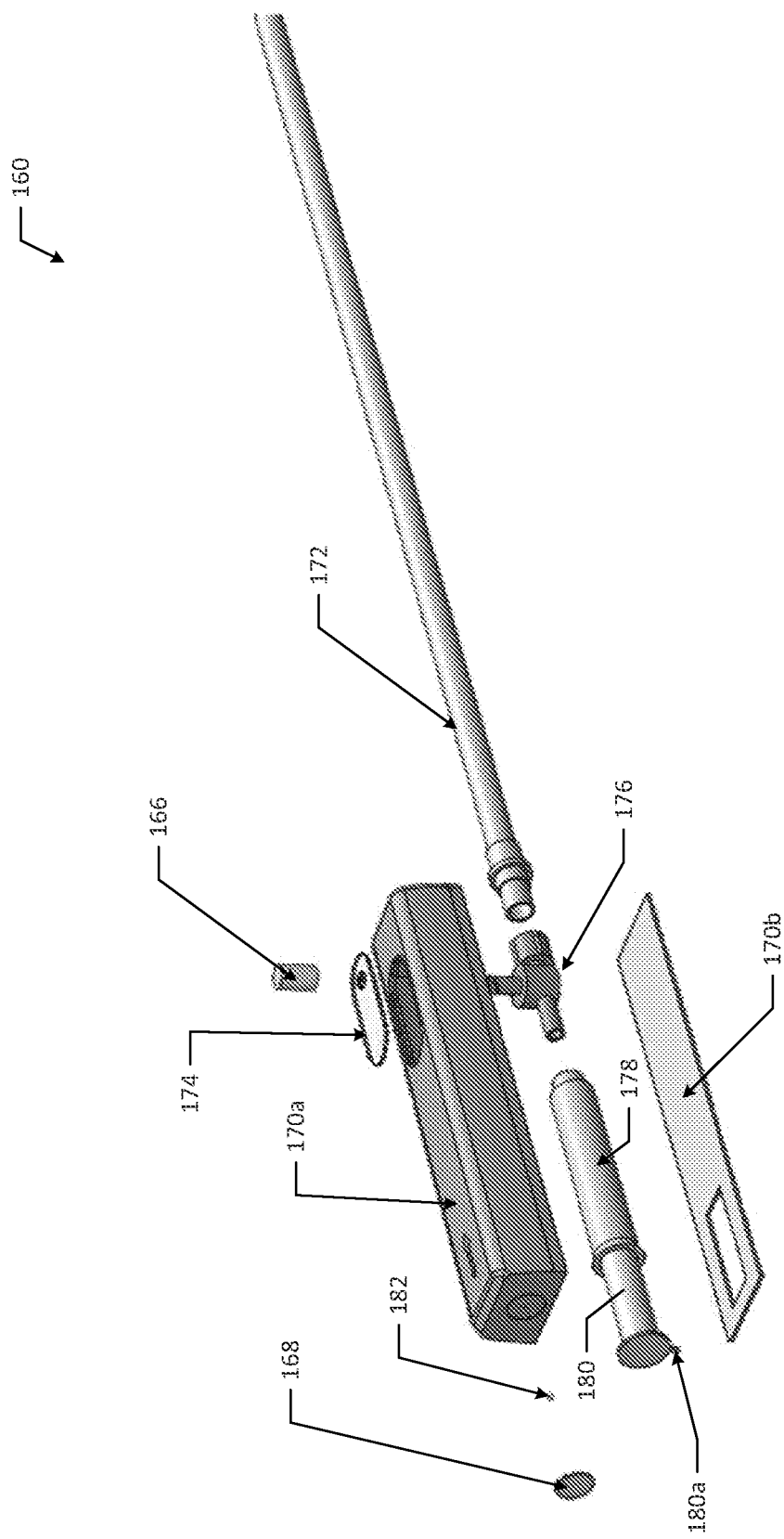
FIG. 4B is an exploded view of the example probe unit of FIG. 4A.

FIG. 4A is a perspective view of an example embodiment of the probe unit 160. FIG. 4B is an exploded view of the probe unit of FIG. 4A. The probe unit 160 extends lengthwise from a proximal end 162 to a distal end 164. The probe unit 160 includes a housing 170 and a cannula 164. The housing 170 is configured to store a sealant (e.g., hemostatic matrix) received via a port (e.g., valve 176) covered by the luer cap 166.

The probe unit 160 also includes an identification tag 168 disposed at the proximal end 162 of the housing 170/the probe unit 160. The identification tag 168 is an electronic device that includes a data store storing identification information (e.g., a number or other identifier) and includes a wireless communication device (e.g., transponder, transceiver, etc.) configured to wirelessly transmit the identification information or identifier to the driver unit 120 when the probe unit 160 is mounted on/attached to the driver unit 120. In an example, the tag 168 is a passive device (e.g., radio frequency identification (RFID) tag, near field communication (NFC) tag) that is powered (e.g., via induction, etc.) by a wireless signal from the driver unit 120 when the probe unit 160 is mounted on/attached to the driver unit 120.

The probe unit 160 also includes a cannula extending away from a distal end 163 of the housing 170 to the distal end 164 of the probe unit 160. The cannula defines a fluid channel for transporting a sealant (e.g., hemostatic agent) from the housing 170 and out of the cannula 172 (at the distal end 164), so that the sealant can be dispensed and/or applied to a biological tissue.

As best shown in FIG. 4B, the housing 170 is formed from a top cover 170a and a bottom cover 170b. When the probe unit 160 is mounted on/attached to the driver unit 120, bottom cover 170b is at a bottom side of the probe unit 160 (adjacent to the driver unit 120) and the top cover 170a is at a top side of the probe unit 160 (opposite the bottom side).

The probe unit 160 also includes a window 174 disposed on the top side of the housing 170 (i.e., at the top cover 170a). In an example, the window 174 includes a transparent substrate (e.g., transparent glass) configured to allow a user to view a portion of an interior of the housing 170.

The probe unit 160 also includes a valve 176, a reservoir 178, and a plunger 180 disposed inside the housing 170 (i.e., between the top cover 170a and the bottom cover 170b). In an example, the valve 176 is a dual check valve that controls flow of a sealant from the filling syringe 102 (shown in FIG. 1) through the top side of the housing (e.g., through a port of the valve 176 that is covered by the luer cap 166 in the illustration of FIG. 4A) and into the reservoir 178. Thus, when filling or refilling the probe unit 160 with sealant fluid, the syringe 102 and the reservoir 178 are in fluid communication via the valve 176. To facilitate dispensing the sealant, the dual check valve 176 controls flow of the sealant from the reservoir 178 to the cannula 172. Thus, the cannula 172 is in fluid communication with the reservoir 178 via the valve 176. When assembled, the cannula 172 and the reservoir 178 are connected to the valve 176.

The plunger 180 is configured to move the sealant out of the reservoir 178 (and/or into the reservoir 178) in response to the plunger 180 being actuated by the driver unit 120. To facilitate this, the plunger 180 includes a snap feature or connector 180a which connects the plunger 180 with the pusher 136 (shown in FIG. 3B) of the driver unit 120.

The probe unit 160 also includes a magnet 182. In an example, the magnet 182 includes any type of permanent magnet disposed at the proximal end 162 of the probe unit 160 (e.g., adjacent to and opposite the hall sensor 146 of the driver unit 120 when the probe unit 160 is mounted on the driver unit 120). The magnet 182 is configured to produce a magnetic field that is detected by the hall sensor 146 when the probe unit 160 is mounted on or attached to the driver unit 120. Referring back to FIG. 3B for example, an interaction of the magnet 182 with the hall sensor 146 enables the controller 150 of the driver unit 120 to detect that the probe unit 160 was attached to and/or mounted on the driver unit 120.

Figure 5:
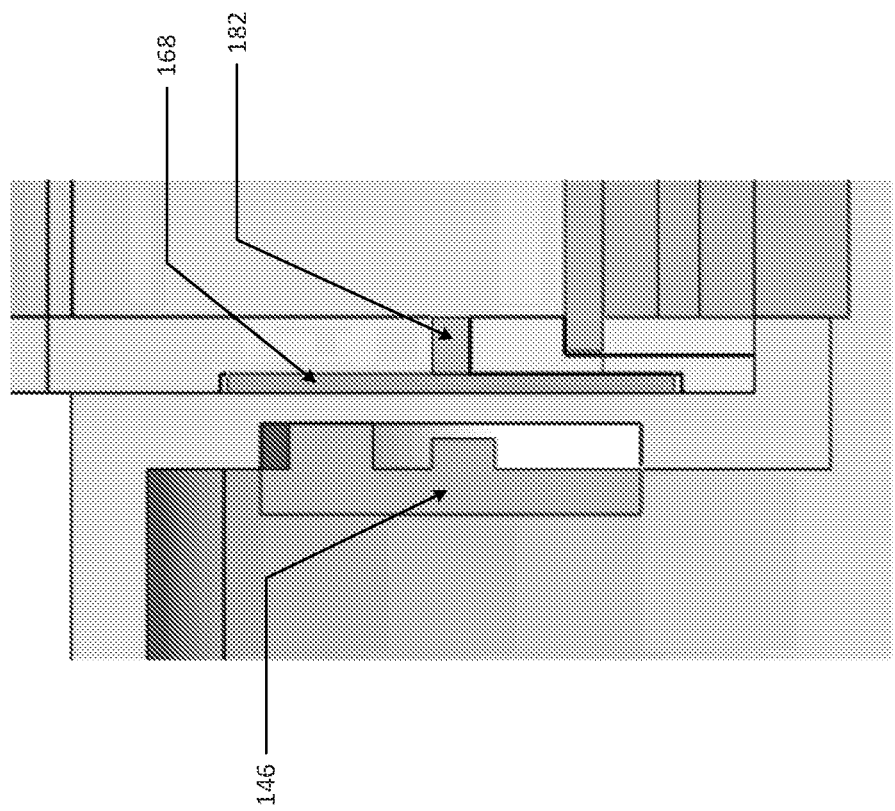
FIG. 5 is a cross-section view of a portion of an example sealant dispenser, according to the present disclosure.

FIG. 5 is a cross section view of a portion of the example dispenser 100, in a configuration where the probe unit 160 is mounted on and/or attached to the driver unit 120. As noted above (and as best shown in FIG. 5), in some examples, when the probe unit 160 is mounted on the driver unit 120, the magnet 182 of the probe unit 160 is disposed adjacent to, within a threshold distance from, and opposite the hall sensor 146 of the driver unit 120. The hall sensor 146 then transmits a signal (e.g., to the controller 150 of the driver unit 120) indicating that the probe unit 160 is mounted on the driver unit 120. The controller 150 may then communicate with the tag 168 to receive an identifier or other identification information identifying the probe unit 160. In an example, the controller 150 then causes the display 130 to display an indication of the identifier received from the tag 168 and/or performs the other functions and operations noted above in the description of the driver unit 120.

Figure 6:
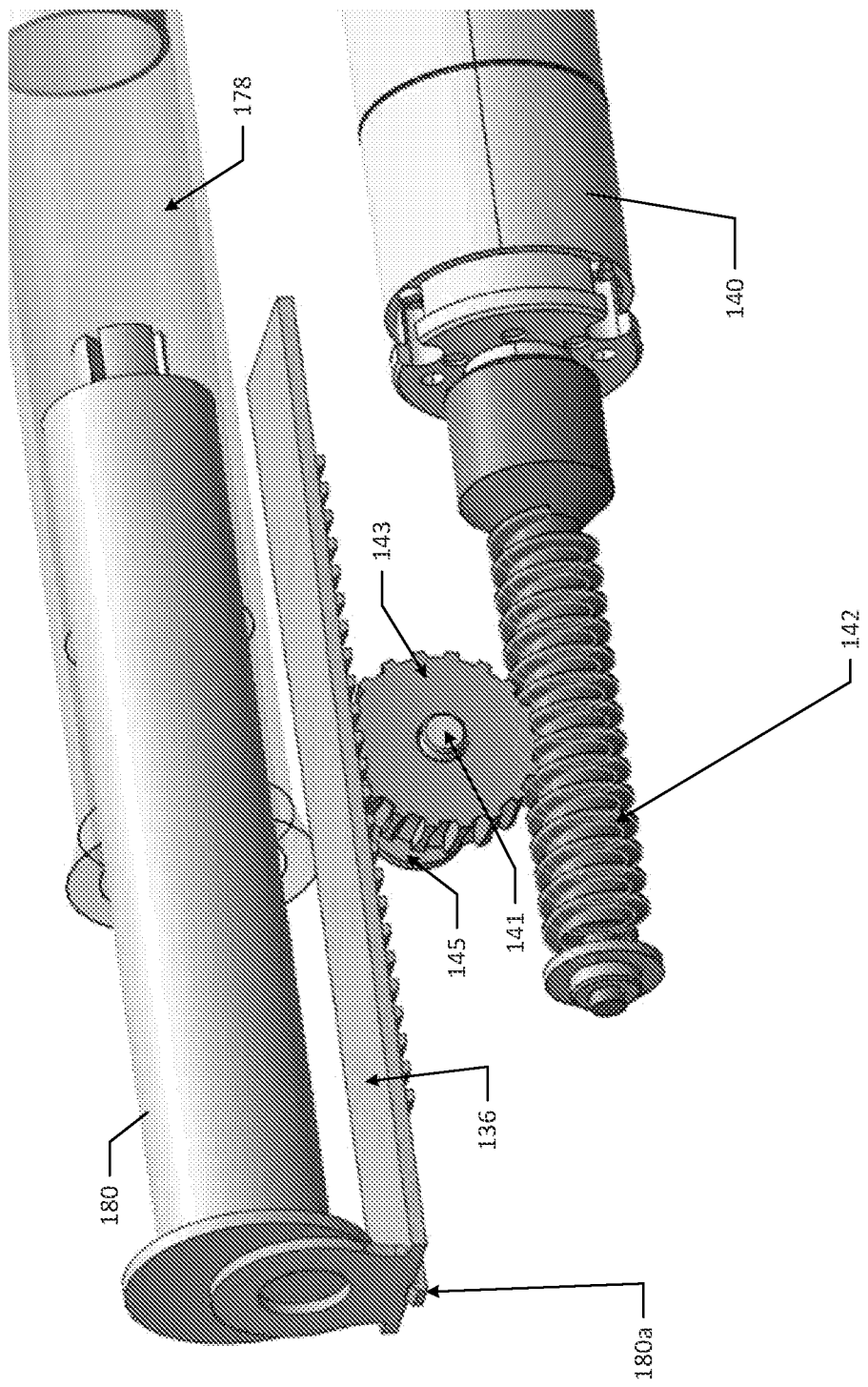
FIG. 6 is a perspective view of another portion of an example sealant dispenser, according to the present disclosure.

FIG. 6 is a perspective view of a portion of the example dispenser 100. It is noted that some of the components of the dispenser 100 are omitted from the illustration of FIG. 6 for convenience in description.

As best shown in FIG. 6, the plunger 180 (of the probe unit 160) is connected to the pusher 136 (of the driver unit 120) via the snap feature or connector 180a.

In the illustrated example of FIG. 6, the driver unit 120 also includes a shaft 141, a gear 143, and a bearing 145. For example, the gear 143 can be configured to transfer an actuation motion of the worm shaft 142 (caused by the motor 140) to the pusher 136 by rotating about the shaft 141. To facilitate this, the gear 143 is attached to the chassis 138 (the chassis shown in FIG. 3B) via the bearing 145.

Although not shown, in some examples, the driver unit 120 also includes an encoder. The encoder may be implemented as a hardware component coupled to the motor 140, as a software component (e.g., executed by the controller 150 shown in FIG. 3B), or as any other circuitry wired to perform the functions of the encoder. In an example, the encoder outputs a signal that indicates an angular position of the motor 140 and/or the worm shaft 142. For example, the signal output from the encoder can be used by the controller 150 (shown in FIG. 3B) to determine an amount of sealant remaining inside the reservoir 178 (of the probe unit 16) and/or an amount of the sealant flowing out of the reservoir 178. For example, the controller 150 can calculate, based on encoder measurements from the encoder, a volume of sealant dispensed by the probe unit 160 due to actuation of the plunger 180 by the motor 140 (via the worm shaft 142, the gear 143, the pusher 136, etc.).

Figure 7:
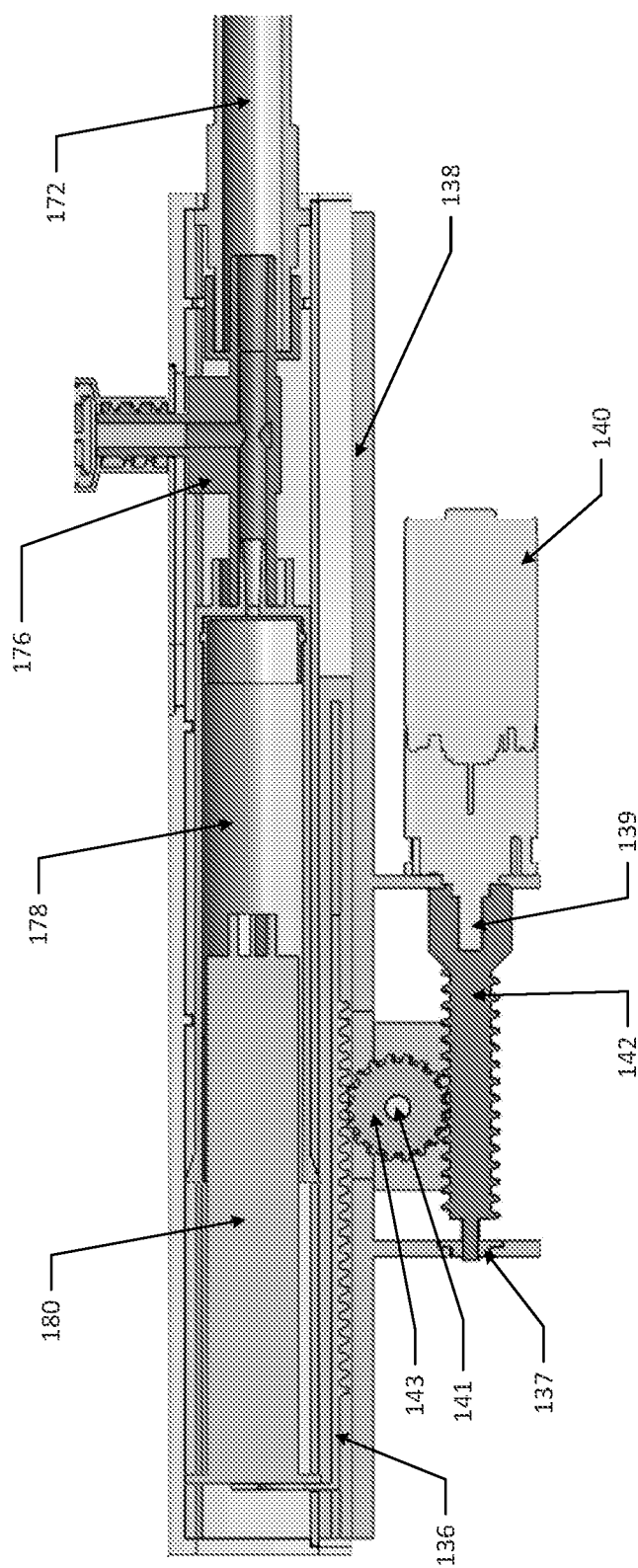
FIG. 7 is a cross-section view of another portion of an example sealant dispenser, according to the present disclosure.

FIG. 7 is a cross section view of a portion of the example dispenser 100, in a configuration where the probe unit 160 is mounted on/attached to the driver unit 120. It is noted that some of the components of the dispenser 100 are omitted from the illustration of FIG. 7 for convenience in description.

As best shown in FIG. 7, the chassis 138 is shaped to support an actuation assembly (e.g., the motor 140, a motor shaft 139, the gear shaft 141, and the gear 143) in a particular arrangement. For example, the driver unit 120 may include a flanged bearing 137 configured to couple an end of the worm shaft 142 with the chassis 138 such that the chassis 138 retains and supports the worm shaft 142 while the motor 140/the motor shaft 139 is rotating the worm shaft 142. In turn, the rotation of the worm shaft 142 causes the gear 143 to rotate, which in turn causes the pusher or rack 136 to push (or pull) the plunger 180 into (or out of) the reservoir 178. For example, when the pusher/rack 136 pushes the plunger 180 into the reservoir 178, a sealant (not shown) in the reservoir may flow from the reservoir 178 to the cannula 172 through the valve 176.

It should be appreciated that for each component with multiple or alternative embodiments, each or any of the embodiments may include the same or similar features as a previously described or a later described embodiment. Additionally, it should be appreciated that some example embodiments herein may include fewer or more components than other example embodiments. Aspects of the subject matter described herein may be useful alone or in combination with one or more other aspects described herein. To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

The many features and advantages of the present disclosure are apparent from the written description, and thus, the appended claims are intended to cover all such features and advantages of the disclosure. Further, since numerous modifications and changes will readily occur to those skilled in the art, the present disclosure is not limited to the exact construction and operation as illustrated and described. Therefore, the described embodiments should be taken as illustrative and not restrictive, and the disclosure should not be limited to the details given herein but should be defined by the following claims and their full scope of equivalents, whether foreseeable or unforeseeable now or in the future.

The invention is claimed as follows:

1. A dispensing device comprising:
   a probe unit that includes:
      a housing configured to receive and store a sealant in a fluid state,
      a cannula extending from a distal end of the housing, the cannula in fluid communication with the sealant stored inside the housing,
      an identification tag configured to wirelessly transmit an identifier that identifies the probe unit, and
      a magnet configured to provide a magnetic field; and
   a driver unit, wherein the probe unit is detachably mounted on the driver unit, the driver unit including:
      at least one rail positioned on a top side of the driver unit and configured to provide a track for receiving and retaining the probe unit when the probe unit is mounted on the driver unit,
      a hall sensor arranged to detect the magnet in response to the probe unit being mounted on the driver unit,
      a controller configured to obtain the identifier from the identification tag of the probe unit in response to the hall sensor detecting the magnet, and
      a display configured to display an indication of the identifier of the probe unit.

2. The dispensing device of claim 1, wherein the probe unit also includes:
   a valve;
   a reservoir configured to store the sealant, wherein the reservoir is in fluid communication with the cannula via the valve; and
   a plunger configured to actuate flow of the sealant from the reservoir to the cannula via the valve.

3. The dispensing device of claim 2, wherein the driver unit also includes:
   a pusher configured to receive and connect with the plunger when the probe unit is mounted on the driver unit;
   a motor coupled to the pusher and configured to actuate the pusher to move the plunger,
   wherein the controller is configured to: generate a control signal for controlling the motor, determine an amount of the sealant inside the reservoir based on the control signal, and cause the display to display the determined amount of the sealant inside the reservoir.

4. The dispensing device of claim 1, wherein the identification tag is a near field communication (NFC) tag.

5. The dispensing device of claim 1, wherein the display is disposed at a proximal end of the driver unit.

* * * * *